Figure 1:
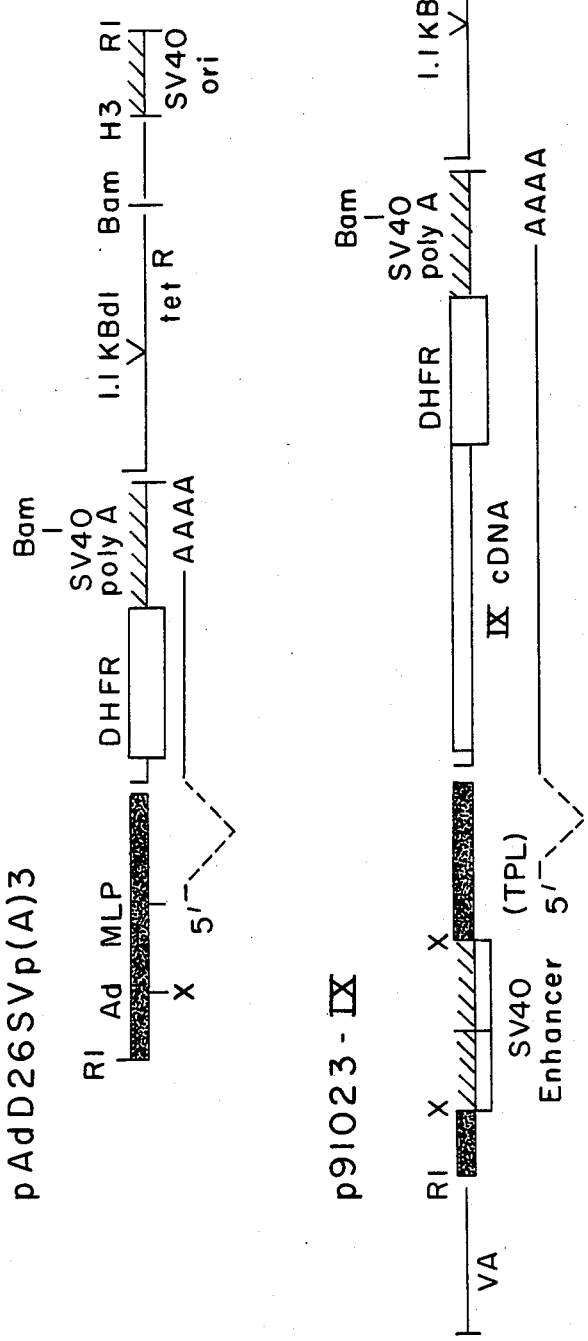

United States Patent [19]

Kaufman et al.

[11] Patent Number: 4,770,999

[45] Date of Patent: Sep. 13, 1988

[54] HIGH YIELD PRODUCTION OF ACTIVE FACTOR IX

[75] Inventors: Randal J. Kaufman, Boston; Charles B. Shoemaker, Belmont; Louise C. Wasley, West Roxbury, all of Mass.

[73] Assignee: Genetics Institute, Inc., Cambridge, Mass.

[21] Appl. No.: 929,294

[22] PCT Filed: Apr. 17, 1986

[86] PCT No.: PCT/US86/00817

§ 371 Date: May 5, 1986

§ 102(e) Date: May 5, 1986

[87] PCT Pub. No.: WO86/06408

PCT Pub. Date: Nov. 6, 1986

Related U.S. Application Data

[63] Continuation-in-part of Ser. No. 725,436, Apr. 22, 1985, abandoned.

[51] Int. Cl.⁴ .................. C12P 21/00; C12P 19/34; C12N 15/00; C12N 1/20
[52] U.S. Cl. .............................. 435/68; 435/70; 435/91; 435/172.3; 435/240.2; 435/317.1; 435/320; 435/253; 536/27; 935/14; 935/55; 935/62; 935/70
[58] Field of Search .............. 435/68, 70, 172.3, 226, 435/253, 240, 317, 320; 935/14, 55, 62, 70; 536/27

[56] References Cited

FOREIGN PATENT DOCUMENTS

| 0162782 | 11/1985 | European Pat. Off. . |
| 0167420 | 1/1986 | European Pat. Off. . |
| 0195592 | 9/1986 | European Pat. Off. . |
| 0200421 | 12/1986 | European Pat. Off. . |
| WO84/00560 | 2/1984 | PCT Int'l Appl. . |
| WO85/05376 | 12/1985 | PCT Int'l Appl. . |
| 2125409 | 3/1981 | United Kingdom . |

OTHER PUBLICATIONS

Kurachi et al., (1982), Proceedings National Academy Sciences, U.S.A., vol. 79, pp. 6461–6464.
Choo et al., (1982), Nature, vol. 299, pp. 178–180.
Fair et al., (1984, Jul.), Blood, vol. 64—pp. 194–204.
Kaufman et al., (1982), Molecular and Cellular Biology, vol. 2, pp. 1304–1319.
Nucleic Acids Res., vol. 11, pp. 2325–2335, 1983, M. Jaye et al.
Embo J., vol. 3, pp. 1053–1060, 1984, D. Ansen et al.
Nature, vol. 315, pp. 683–685, 1985, D. Ansen et al.
Nature, vol. 316, pp. 268–270, 1985, H. De La Salle et al.
Nature, vol. 316, pp. 271–273, 1985, S. Busby et al.
Proc. Natl. Acad. Sci., U.S.A., vol. 76, pp. 4990–4994, K. Katayama et al.

Primary Examiner—Thomas G. Wiseman
Assistant Examiner—S. Seidman
Attorney, Agent, or Firm—Bruce M. Eisen; Mary Bak; Brian P. O'Shaughnessy

[57] ABSTRACT

High yields of active Factor IX are produced by culturing a CHO cell line transfected with chromosomally-integrated Factor IX cDNA in medium to which vitamin K is added.

6 Claims, 1 Drawing Sheet

HIGH YIELD PRODUCTION OF ACTIVE FACTOR IX

This is a continuation-in-part of U.S. application Ser. No. 725,436, filed Apr. 22, 1985, now abandoned.

This invention relates generally to the cloning and expression in high yield of Factor IX, and more particularly, to the production of biologically-active Factor IX by means of culturing mammalian cells into media containing vitamin K which Factor IX cDNA has been chromosomally-integrated.

The plasma glycoprotein, Factor IX, plays a critical role in the blood-clotting process. Normally synthesized in the liver, Factor IX requires vitamin K activity for the γ-carboxylation of its 12 amino-terminal glutamic acid residues. A deficiency of Factor IX in the body characterizes a type of hemophilia (type B). Treatment of this disease is presently limited to intravenous tranfusion of human plasma protein concentrates of Factor IX. However, in addition to the practical disadvantages of time and expense, transfusion of blood concentrates involves the risk of transmission of viral hepatitis, acquired immune deficiency syndrome or thromboembolic diseases to the recipient. An alternative method of producing Factor IX, other than extraction from human plasma, is therefore highly desirable.

The application of recombinant DNA techniques to the production of Factor IX has elicited considerable information about the protein. The cDNA coding for human Factor IX has been isolated, characterized, and cloned into expression vectors. See, e.g., K. H. Choo et al, "Molecular Cloning of the Gene for Human Antihemophilic Factor IX', Nature, Vol. 299: 178-180 (September 1982) and K. Kurachi et al, "Isolation and Characterization of a cDNA Coding for Human Factor IX," Proc. Natl. Acad. Sci. U.S.A., Vol. 79: 6461-65 (November 1982).

PCT patent application WO No. 84/00360 published Feb. 16, 1984 describes the identification and cloning of a human Factor IX nucleotide sequence or fragments thereof for use primarily as diagnostic probes. This application only prophetically refers to the production of a human Factor IX polypeptide through growth in mammalian tissue culture cells, preferably a hepatoma cell line. The inventions' subsequent article, D. S. Anson et al, "Expression of Active Human Clotting Factor IX from Recombinant DNA Clones in Mammalian Cells" Nature, Vol. 315, pp 683-685 (June 20, 1985), describes the production of very low levels of a purportedly active human Factor IX polypeptide from a transformed rat hepatoma cell line. (See page 685, column 1)

European patent application No. 162,782, published Nov. 11, 1985, refers to construction of a recombinant viral vector containing a sequence coding for human Factor IX. Biologically active human Factor IX in low yields is assertedly obtained from bacterial cells containing the episomally integrated recombinant Factor IX sequence. The influence of viral components on growth of the host cells and glycoprotein of the protein however can result in unreliable and varied batches of protein. [See, also H. de la Salle et al, "Active γ-carboxylated human Factor IX expressed using recombinant DNA techniques," Nature, 316: 268-270 (July 18, 1985)]

Another recent report, S. Busby et al. "Expression of active human Factor IX in transfected cells," Nature, 316: 271-273 (July 18, 1985) also refers to expression of low levels of recombinant Factor IX in BHK cells cotransfected with a neo gene marker.

Even these recent studies therefore demonstrate the continued difficulty in obtaining a stable system for producing high yields of Factor IX in biologically active and reliably consistent form.

In accordance with the present invention it is surprisingly discovered that high yields of biologically active Factor IX protein can be produced by culturing a CHO cell line containing chromosomally integrated Factor IX cDNA and adding heterologous vitamin K to the culture medium for a predetermined time prior to harvesting the polypeptide. Even cells that have not previously been demonstrated to provide γ-carboxylation, can be shown to provide active Factor IX by this method.

Vitamin K is added to the culture medium in the form of K1 or K3. Where K3 is the vitamin of choice, a concentrate of from about 0.1 ng to 10 ug of vitamin can be added per ml of cell culture, with the preferred concentration range of between 5 ng to 10 ug. Alternatively, vitamin K1 may be added in a desired concentration range of between about 10 ng to 50 ug of vitamin per ml of media or preferably 100 ng to 100 ug of vitamin per ml of media.

The length of time required to produce the maximum quantity of active Factor IX can be easily determined by simple experimentation, i.e. analyzing aliquots of conditioned medium at various time intervals for the amount of active Factor IX present until the maximum concentration is determined.

In another embodiment of the present invention, other biologically active blood coagulation proteins and plasma proteins containing gamma-carboxyglutamic acid are produced from cells transformed with chromosomally-integrated cDNA coding for such proteins by adding vitamin K to the cell culture medium. Examples of such blood coagulation proteins and plasma proteins produced in biologically active form from cDNA in accordance with the present invention include prothrombin, Factor X, Factor VII, Protein C, Protein S, and the like.

The biologically active Factor IX produced by the eucaryotic expression of the cloned Factor IX gene in accordance with the present invention can be used for the in vivo treatment of humans by physicians. The amount of active ingredient will, of course, depend upon the severity of the condition being treated, the route of administration chosen, and the specific activity of the active Factor IX.

The active Factor IX produced according to the present invention may be administered by any route and in any pharmaceutical formulation and dosage which are typical for the natural serum-derived Factor IX. Desirably, the route, formulation and dosage regimens will take into account differences in activity, if any, between the natural Factor IX and the protein produced as described herein.

The following examples refer to the initial isolation and cloning of the Factor IX cDNA, sequencing thereof and the preparation of an expression vector system capable of expression active Factor IX.

FIG. 1 illustrates the structure of expression plasmids p91023-IX and pAaD26SVpA3.

EXAMPLE 1

Isolation of human Factor IX cDNA clones

A unique oligonucleotide with the sequence 5'pGTACAGGAGCAAACACC-3'OH was synthesized which was homologous to Factor IX RNA approximately 475 bp downstream from the initiator codon (Kurachi et al., 1982 supra; Choo et al., 1982, supra). This oligonucleotide was labeled at the 5' end using polynucleotide kinase (New England Biolabs) and Y-$^{32}$P-ATP (New England Nuclear). Human liver double-stranded cDNA was prepared (Maniatis et al., *Molecular Cloning, A Laboratory Manual*, Cold Spring Harbor, 1982) and inserted into a GT10 vector as described by Toole et al., *Nature*, 313: 342-347, (1984). Approximately 100,000 recombinant phage plaques were screened on duplicate filters with the labeled oligonucletide probe by the method of Woo et al., *Proc. Nat'l. Acad. Sci USA*, 75: 3688-3692, (1978). Hybridization was at 42° C. for 40 hours in 5X SSC, 5X Denhardt's, 0.5% by weight SDS and 10 mM EDTA and washed extensively at 42° in 2X SSC. Duplicate positives were plaque purified and DNA was prepared from plate stocks [Maniatis et al., (1982), supra] and analyzed by restriction digestion.

EXAMPLE 2

Isolation of human Factor IX genomic clones

Three human genomic libraries were screened using human Factor IX cDNA nick-translated probes by the method of Benton, et al., *Science*, 196: 180-182 (1977). The first library screened was an amplified HaeIII/AluI partial library in Charon 4A [Lawn et al., *Cell*, 15: 1157-1174, (1978)]. The second library was prepared by the method described by Maniatis et al., (1982) supra using a Sau3A partial digest cloned into Charon 28. A third library was prepared from the human lymphoblastoid line GM1202A (NIGMS mutant cell repository) which contains four X chromosomes. In this case Sau3A partial DNA was cloned as above into J1 (kindly supplied by J. Mullins) a derivative of L47.1 [Loenen, et al., *Gene* 10: 249 (1980)] in which polylinkers have been inserted replacing the two small EcoR1-BamH1 fragments. Positive hybridizing plaques were purified and the phage DNA prepared following $C_sCl_2$ step gradient purification of a one liter liquid lysate [Maniatis et al., (1982), supra].

EXAMPLE 3

DNA sequence analysis

DNA sequences were obtained following subcloning into M13 phage vectors [Norrander et al., *Gene*, 26: 101-106 (1983)] by the dideoxy chain termination method [Sanger et al., *Proc. Nat'l. Acad. Sci. USA*, 74 5463-5467 (1977)] using synthetic oligonucleotide primers. The Factor IX cDNA was subcloned into M13 vectors following an ExoIII generated series of deletions according to the following procedures.

A plasmid containing the region to be sequenced is digested with a restriction enzyme which cuts at a unique site to one side of the region to be sequenced. The DNA (approximately 20 ug) is ethanol precipitated and dissolved in 100 ul of a solution containing 50 mM Tris, pH 8.0, 1 mM MgCl$_2$, 1 mM 2-mercaptoethanol (ExoIII buffer). The tube is warmed to 30° C. and 200 units of ExoIII (Pharmacia P-L Biochemicals) are added. Based on the estimated degradation rate under these conditions of approximately 200 base pairs/min/end, aliquots are quenched at 30 second intervals thereby generating ends throughout the region to be sequenced. The aliquots are quenched by pooling into a tube containing 300 ul of a solution containing 500 mM NaCl and 20 mM EDTA, pH 8.0 (Exo quench). The deleted DNA is ethanol precipitated and dissolved in 80 ul of H$_2$O. Mild S1 digestion is initiated by the addition of 80 ul of a solution containing 60 mM sodium acetate, 2 mM ZnSO$_4$, 500 mM NaCl, 10% by weight glycerol, pH 4.6 and 50 units S1 nuclease (Sigma). After 15 minutes at 20° C. the reaction is quenched with 40 ul of 500 mM Tris-HCl, 1M NaCl, pH 8.0 and ethanol precipitated. Blunt ends are created by subsequent treatment with 5 units of Klenow fragment of DNA polymerase (BRL) in a 100 ul solution containing 10 mM Tris-HCl, 10 mM MgCl$_2$, 10 mM 2-mercaptoethanol, 100 uM dXTP's (containing dATP, dCTP, dGTP, dTTP), pH 7.5 at 37° C. for 15 minutes. The reaction is phenol extracted and the solution centrifuged through a 1 ml G50 spin column (prepared in a 1 ml syringe in 10 mM Tris, pH 8.0) to recover 100 ul.

The DNA is ethanol precipitated and then digested by a restriction enzyme (that leaves "sticky" ends) which cuts on the opposite end of the region to be sequenced than the original restriction cut site prior to ExoIII. Following digestion, the DNA fragments are resolved in a Tris-acetate agarose gel. Gel slices which correspond to approximately 200 bp size classes throughout the size range desired are removed. One fragment end would be from an ExoIII generated blunt end within the region to be sequenced and the other end from the re-cut site. The DNA fragments are purified by glass powder affinity [Volgelstein and Gillespie, *Proc.-Nat'l. Acad. Sci. USA*, 76: 615-619 (1979)] following dissolution in NaI.

These DNA fragments are then ligated into M13 cloning vectors in an asymmetric manner wherein the blunt end is nearest the universal primer binding site. M13 recombinant plaques which hydridize to a probe made specifically for the region over which sequence is desired are selected for subsequent preparation of single-stranded template DNA [Sanger et al., (1977), supra]. Generally it is necessary to sequence with universal primer only one or two isolates from each size class to obtain overlapping sequence covering the entire region to be sequenced up to 4 kb. Second-strand sequence can be obtained by repeating the procedure, deleting from the opposite side of the region to be sequenced.

EXAMPLE 4

Recombination of Factor IX cDNA with Factor IX Exon 1

A 4.5 kb HindIII fragment containing the Factor IX promoter and 5' coding region was cloned into Charon 21A. A 2.5 kb fragment of Factor IX cDNA containing the entire Factor IX coding sequence from the eleventh codon of the signal sequence coding region to the XbaI site 66 bp from the polyA tail was subcloned into AN7 plasmid (a derivative of VX). [See Maniatis et al., (1982), supra]. There were 57 bp of exon 1 sequence within the Factor IX cDNA. The exon 1 containing Charon 21A phage were plated on bacteria harboring the recombinant AN7 plasmid and subsequently harvested as a plate stock. Phage which had recombined with the supF containing AN7 plasmid could now be selected by plating onto the supF$^-$ bacterial line W3110 [Maniatis et al., (1982), supra]. Approximately one in $2\times10^4$ phage were supF$^+$. One isolate was chosen for large scale DNA preparation and shown by restriction mapping and subsequent sequence analysis to have recombined correctly with the AN7 plasmid within the 57 bp region of homology to obtain a Factor IX "mini gene".

EXAMPLE 5

Exonucleolytic removal of 5' non-coding sequence

The 2.3 kb Xba fragment containing the Factor IX "mini gene" was purified from AN7 by glass powder affinity. Approximately 5 ug of the fragment was digested with 50 units of ExoIII in 40 ul of ExoIII buffer. After 1 minute, 8 ul aliquots were removed to 120 ul of Exo quench at 15 second intervals. The DNA was treated with exonuclease S1 nuclease and Klenow fragment of polymeyase 1 as above and then ligated to Pst adapters 5'p-CT AGAGGCCT CT GCA
GAT CT CCGGAG—OH 5'

The adapted DNA was then put onto a Tris-acetate agarose gel and DNA of approximately 2.3 kb was purified by glass powder affinity and ligated into a M13mp11 Pst vector. Recombinant plaques were screened with an oligonucleotide homologous to the first 17 bp of Factor IX coding sequence RNA. Positive hybridizing plaques were sequenced with the same oligonucleotide to find the deletion end point at the 5' end of the gene. Universal primer sequencing determined the 3' deletion end point. The entire sequence of the biologically active recombinant Factor IX cDNA is shown in Table I below.

TABLE I

| CAATCTGCTA | GCAAAGGTT | | ATGCAGCGCG | TGAACATGAT | CATGGCAGAA | TCACCAGGCC |
|---|---|---|---|---|---|---|
| TGATCACCAT | CTGCCTTTTA | GGATATCTAC | TCAGTGCTGA | ATGTACAGTT | TTTCTTGATC | ATGAAAACGC |
| CAACAAAATT | CTGAATCGGC | CAAAGAGGTA | TAATTCAGGT | AAATTGGAAG | AGTTGTTCA | AGGGSCCTT |
| GAGAGAAAT | GTATGGAAGA | AAAGTGTAGT | TTTGAAGAAG | CACGAGAAGT | TTTTGAAAAC | ACTGAAAGAA |
| CAACTGAATT | TGGAAGCAG | TATGTTGATG | GAGATCAGTG | TGAGTCCAAT | CCATGTTAA | ATGGCGCAG |
| TTGCAAGGAT | GACATTAATT | CCTATGAATG | TTGGTGTCCC | TTTGGATTTG | AAGGAAAGAA | CTGTGAATTA |
| GATGTAACAT | GTAACATTAA | GAATGCAGA | TGCGAGCAGT | TTTGTAAAAA | TAGTGCTGAT | AACAAGGTGG |
| TTGCTCCTG | TACTGAGGGA | TATCGACTTG | CAGAAAACCA | GAAGTCCTGT | GAACCAGCAG | TGCCATTTCC |
| ATGTGGAAGA | GTTTCTGTTT | CACAAACTTC | TAAGCTCACC | CGTGCTGAGA | CTGTTTCC | TGATGTGGAC |
| TATGTAAATT | CTACTGAAGC | TGAGATGCCA | TTGGATAACA | TCACTCAAAG | CAGGTTGTTT | TTTAATGACT |
| TCACTCGGT | TGTTGGTGGA | GAAGATGCCA | AACCAAGGTCA | ATTCCCTTGG | CTGCTGCCCA | TGAATGGTAA |
| AGTTGATGCA | TTCTGTGGAG | GCTCTATCGT | TGGATTGTAA | TGGATTGTAA | AGAACATACA | CTGTGTTGAA |
| ACTGGTGTTA | AAATTACAGT | TGTCGCAGTT | GAACATAATA | TTGGGAGAC | AAGTACAACC | GAGCAAAAGC |
| GAAATGTGAT | TGAATTATT | CCTCACCACA | ACTCACCACA | AGCTATTAAT | TTTGCATTGC | ATGACATTGC |
| TACACGAACA | CTGGACGAAC | AAACAGCTAC | GTTACACCTA | GTTGCATTGC | AAGAGTCTTC | TGACAAGGAA |
| CCTTCTGGAA | TCTTCCTCAA | CCTTAGTGCT | GGCTATGTAA | GTGGCTGGGG | AAGAGTCTTC | CACAAGGGA |
| GATCAGCTTT | AGTTCTTCAG | ATTTGGATCT | TTCCACTTGT | TGACCGAGCC | ACATGTCTTC | GATCTACAAA |
| GTTCACCATC | TATAACAACA | TACCTTAGAG | TGGTTCTGTG | GAAGGAGGTA | GAGATTCATG | CAAGGAGAT |
| AGTGGGGAC | CCCATGTTAC | TGAAGTGGAA | GGGACCAGTT | TCTTAACTGG | AATTAACTGG | TGGGTGAAG |
| AGTGTGCAAT | GAAAGGCAAA | TATGGAATAT | ATACCAAGGT | ATCCCGGTAT | GTCAACTGGA | TTAAGGAAAA |
| | | | | | | |
| AACAAAGCTC | ACT TAA | | TGAAAGATGG | ATTTCCAAGG | TTAATTCATT | GGAATTGAAA |
| | | | | | | |
| ATTAACAGGG | CCTCTCACTA | ACTAATCACT | TTCCCATCTT | TTGTTAGATT | TGAATATATA | CATTCTATGA |
| TCATTGCTTT | TTCTCTTTAC | AGGGAGAAT | TTCATATTTT | ACCTGAGCAA | ATTGATTAGA | AAATGAACC |
| ACTAGAGGAA | TATAATGTGT | TAGGAAATTA | CAGTCATTTC | TGAAGCCCAG | CCCTTGACAA | AATTGTGAAG |
| TTAAATTCTC | CACTCTGTCC | ATCAGATACT | ATGGTTCTCC | ACTATGGCAA | CTAACTCACT | CAATTTTCCC |
| TCCTTAGCAG | ATCCCATCT | TCCCGATCTT | ATGGTCTCTC | CCAACAAAA | CATCATGTTT | ATTAGTTCTG |
| TATACAGTAC | AGGATCTTTG | GTCTACTCTA | CTTGCTTCT | GCTCAGTACC | ACACTCATGA | AGAAAGAACA |
| CAGGAGTAGC | TGAGAGGCTA | AAACTCATCA | TCACGAGAAG | CCTTTTCCT | CTACCCTATT | CCTCAATCTT |
| TTACCTTTTC | CAAATTCCAA | ATTCCCCAAA | AAACACTAC | TCTTCTTTC | CCCTCCTCTC | CCTTTACCC |
| TCCATGGTAG | CCATGTCTAT | GATGGGGAGC | TCAGTTTTAC | TATACTTCTG | TACAGTTA | TACATGTCTA |
| TCAAACCCAG | CAAATTCAAC | ATAGTGGAGA | CTTGCTTTC | AGAACATAGG | GATGAAGTAA | GGTGCCTGAA |
| AAGTTTGGGG | ACTTGCTTCC | TTTCAGAGAG | TTAAGTTATT | TATATATAT | AATATATATA | TAAAATATA |
| AATATACAAT | GAAAGTTTC | AGTGTGTG | TGTATGCGTG | TGTGTAGACA | CACACGCATA | CACACATATA |
| ATGAAGCAA | ATATATATAT | TTAAGAGCTT | GTATGGTTAT | GGAGGTCTGA | CTAGGCATGA | TTTCACGAAG |
| GCAAGATTGG | TAAGCCATTC | GTAACTAAAA | AAGCTGACAT | TGACCCAGAC | ATATTGTACT | CTTTCTAAAA |
| ATAATAATAA | CATATCAGTT | AGAAAGAAGA | GAACCGTTCG | TTTGCAATCT | ACAGCTAGTA | GAGACTTGAG |
| GAAGAATTCA | ACAGTGTGTC | TTCAACTAGC | TCATGTGCCA | AGCAAGAAGT | TGAAGTTGCC | TAGACCAGAG |
| GACATAAGTA | TCATGTCTCT | TTTAACTAGC | ATACCCGAA | GTGGAGAGG | ATGCAGCAGG | CTCAAAGGCA |
| TAAGTCATTC | CAATCAGCA | ACTAAGTTGT | CCCTTTCTGG | TTTCGTGTTC | ACCATGGAAC | ATTTGATTA |
| TAGTTAATCC | TTCTATCTTG | AATCTTCTAG | AGAGTTGCTG | AGAGTTGCTG | ACCATGTAAC | CTTGTGAAT |
| TAATAAACTG | GTGTTCTGGT | TCAAAAAAAA | AA | | | |

[Start and stop codons are underlined. The coding region is separated from the 3' and 5' untranslated regions by a space.]

EXAMPLE 6

Monitoring Factor IX Expression

To prepare samples for the following Factor IX assay, approximately $4 \times 10^6$ logarithmically glowing cells were rinsed four times (5 ml each) with serum-free media containing additions as indicated. After 24 hours at 37° C. samples were taken, frozen in a dry ice/ethanol bath, and stored at 70° C. until assayed.

A. Factor IX Elisa

Microtitre plates were coated with human Factor IX murine monoclonal antibody (Hybritech). The plates were washed, and sample or standard Factor IX preparations were added after dilution into alpha media. The Factor IX standard was purified human Factor IX diluted from 4.0 ug to 1.0 ng. The secondary antibody (rabbit anti Factor IX, Calbiochem) was applied and washed, and alkaline phosphatase conjugated goat anti-rabbit IgG (Zymea) was applied. The substrate was alkaline phosphate table (Sigma #104) diluted in diethanolamine and results were read at 410 nm.

B. Factor IX Clotting Assays

The one stage activated partial thromboplastin time assay as described by R. Biggs, *Human Blood Coagulation Haemostasis and Thrombosis* (Ed. 1), Oxford, Blackwell, Scientific, pg. 614 (1972) was carried out with equal volumes of: (1) activated partial thromboplastin reagent (general diagnostics) (2) Factor IX deficient plasma (George B. King Biomedical) and (3) normal pooled plasma as standard (George B. King Biomedical) or the sample. One unit of activity is defined as that amount present in 1 ml of normal pooled plasma.

EXAMPLE 7

Expression of Factor IX in Mammalian Cells

The Factor IX coding sequence was inserted into the Pst 1 site of plasmid p91023 (A) which is described in Example 3 of Japanese patent publication No. 12288/86, published Jan. 20, 1986 which corresponds to U.S. patent application Ser. No. 677,813, filed Dec. 4, 1983. The resulting clones are screened for proper orientation of the Factor IX gene with those having proper orientation selected as p91023-IX. The Factor IX expression vector, p91023-IX, contains the SV40 enhancer upstream from the AdMLP, a cDNA copy of the adenovirus tripartite leader (TPL), the adenovirus VA genes, [Kaufman, PNAS, 82: 689–693 (1985)], and the inserted Factor IX cDNA coding region upstream from the DHFR coding region. EcoR1(R1), BamH1(bam) and Xho1(X) restriction sites are indicated. The DHFR expression vector, pAdD26SVpA(3) [Kaufman, et al., *Mol. Cell. Bio.*, 2: 1304–1309 (1982)], contains the adenovirus major late promoter including the first late leader and 5' splice site. The leader exon from the RNA transcript is spliced properly to an introduced 3' splice site. The vector contains the SV40 early polyadenylation site, 2.7 KB derived from pSVOa [Mellon et al., *Cell,* 27: 279–288 (1981)] which contains the ColE1 origin of replication, a pBR322 derivative lacking sequences detrimental to replication in mammalian cells, tetracycline resistance, and the SV40 origin of replication.

The Factor IX expression vector p91023-IX was introduced with pAdD26SVpA3, into DHFR deficient Chinese hamster ovary cells by calcium phosphate mediated DNA transfection. (See FIG. 1.) Cells selected for the DHFR positive phenotype expressed Factor IX at a low level. Then the transformants were pooled and selected for growth in the following sequentially increasing concentrations of methotrexate (MTX), i.e., 0.02, 0.1, 0.5, 1.0, 5.0 and 20 uM. Cells selected in this manner contain amplified copies of the introduced DHFR genes as well as amplified Factor IX genes. The amplified genes were generally localized to one or two specific chromosomes [Kaufman et al., *Mol. Cell. Bio.* 3, 699–711 (1983)].

DUKX B11 DHFR deficient CHO cells (Urlaub, et al, *Proc. Nat'l Acad. Sci.* 77: 4210–4220, 1980; Kaufman, et al, *J. Mol. Biol.* 159: 601–621, 1982) were transfected with a mixture of 25 ug of p91023-IX and 2.5 ug of pAdD26SVpA3 (Kaufman & Sharp, op. cit) by calcium-phosphate. Transformants were selected in media lacking nucleosides as described (Kaufman & Sharp, op. cit). A similar transfection which gave similar results included the addition of 2.5 ug of pSV2 Neo [Southern, et al, *J. Mol. Appl. Genet.*, 1: 327–341 (1982)]. For the latter transfection, the DHFR+ transformants were initially selected in media lacking nucleosides with the addition of the antibiotic G418 (1 mg/ml) in order to select for the pSV2 neo marker. The addition of a G418 resistance marker can be useful to facilitate transfer of chromosomes containing transfected DNA into other cells where selection directly for the amplified DHFR gene copies is not possible.

Initial transformants were pooled (approximately 25 transformants/pool) and subjected to growth in increasing concentrations of MTX. These pools were analyzed for Factor IX expression by $^{35}$S-methionine labeling and immune precipitation of the conditioned media and cell extracts with a monoclonal antibody which recognizes human Factor IX. A band of approximately 55k daltons was observed in the cell extracts and its level increased as cells were selected for higher degrees of MTX resistance. When the conditioned medium was similarly analyzed, a heterogenous smear was observed which ranged from 72 k daltons down to 55 k daltons. The smear heterogeneity is likely due to the heterogeneity of glycosylation of the secreted material. In addition, the level of the secreted Factor IX antigen determined by Elisa increased approximately 3000-fold upon selection to 20 um MTX. (See Table II) The level of Factor IX antigen (i.e. not biologically active) in the 5α3 pool of cells was determined to be 43.4 ug/ml.

TABLE II

Factor IX antigen in conditioned medium of cells selected for growth in increasing concentrations of MTX.

|  |  | [MTX] | UG/ML |
|---|---|---|---|
| POOL | 5 α 3 | 0 | 0.015 |
|  | 5 α 3 | 0.02 | 0.15 |
|  | 5 α 3 | 0.1 | 6.9 |
|  | 5 α 3 | 0.5 | 29.4 |
|  | 5 α 3 | 5.0 | 36.0 |
|  | 5 α 3 | 20.0 | 43.4 |

EXAMPLE 8

Expression of Factor IX activity in CHO cells

When the conditioned media from the Factor IX producing CHO cells (5α3 in various concentrations of MTX) was analyzed for Factor IX activity, there was no activity detected above background. Vitamin K was added to the medium containing the CHO cells which produce Factor IX antigen. Table III shows the results of monitoring Factor IX activity after adding increasing concentrations of vitamin K1 (3-phytylmenadione, Sigma) to the CHO Factor IX producing cells (5α3, 20 um MTX) for 24 hours. Significantly, as the concentration of vitamin K1 increased to 5 ug/ml, so did the Factor IX activity in the conditioned medium. Vitamin K1 had no effect on activity when added back to conditioned media immediately before the assay. Thus, in the presence of vitamin K1, the CHO cells produced up to 0.275 units of active Factor IX/ml/day/$10^6$ cells.

To determine the validity of a concern that very little of the fat soluble vitamin K1 was actually being delivered to the cell, a similar effect has been demonstrated for the water soluble derivative vitamin K3 (menadione, Sigma). Lower levels of K3 are required for maximal activity (0.005 ug/ml) to be obtained with vitamin K. The specificity of the vitamin K3 dependence on Factor IX activity was demonstrated by adding warfarin (at 1 ug/ml), a specific antagonist of vitamin K, which blocked the appearance of active Factor IX.

TABLE III

| Factor IX activity v. vitamin K1 | | |
|---|---|---|
| Cells | Vitamin K1 | m Units/ml/day |
| 5 α 3 (20 um) | 100 ng/ml | 42.5 |
| 5 α 3 (20 um) | 500 ng/ml | 105.0 |
| 5 α 3 (20 um) | 1 ug/ml | 192.0 |
| 5 α 3 (20 um) | 5 ug/ml | 275.0 |
| 5 α 3 (20 um) | 10 ug/ml | 268.0 |
| CHO | 5 ug/ml | 17.5 |

Thus the specific activity of factor from the CHO cells is 16.5 mU/ug of Factor IX. Since the level of Factor IX in normal plasma is 1 unit/ml/5 ug of Factor IX protein, the specific activity (units of Factor IX activity/mg of Factor IX protein from CHO cells is 9% that derived from normal plasma.

The present invention has been described in detail including the preferred embodiments thereof. However, it will be appreciated that those skilled in the art may make modifications and improvements within the spirit and scope of this invention which is defined by the appended claims.

What is claimed is:

1. A method for producing biologically active human Factor IX in high yield comprising culturing a CHO cell line transfected with chromosomally-integrated Factor IX cDNA in medium containing vitamin K.

2. The method according to claim 1, wherein vitamin K is selected from the group consisting of vitamin K1 and vitamin K3.

3. The method according to claim 2, wherein said medium comprises a concentration of about 0.1 ng to 50 ug vitamin K3/ml medium.

4. The method according to claim 3, wherein said medium comprises a concentration of about 5 ng to about 10 ug vitamin K3/ml medium.

5. The method according to claim 2, wherein said medium comprises a concentration of about 10 ng to about 50 ug vitamin K1/ml medium.

6. The method according to claim 5, wherein said medium comprises a concentration of about 100 ng to about 100 ug vitamin K1/ml medium.

* * * * *

UNITED STATES PATENT AND TRADEMARK OFFICE
CERTIFICATE OF CORRECTION

PATENT NO. : 4,770,999

DATED : September 13, 1988

INVENTOR(S) : Kaufman et al.

It is certified that error appears in the above-identified patent and that said Letters Patent is hereby corrected as shown below:

Columns 7 and 8 of the above-referenced patent, please make the following corrections:

Line 3, Column 7, change "AGGGSSCCTT" to --AGGGAACCTT--

Line 11, Column 1, change "TCACTCGGT" to --TCACTCGGGT--

Line 11, Column 3, change "AACCAAGGTCA" to --AACCAGGTCA--

Line 13, Column 4, change "TTGSGGAGAC" to --TTGAGGAGAC--

Line 31, Column 5, change "AGAAACATAGG" to --AGAACATAGG--

Line 32, Column 7, change "TAAAATATA" to --TAAAATATAT--

Line 40, Column 6, change "GTATGTTCC" to --GTATGTTTCC--

Signed and Sealed this

Fifteenth Day of August, 1995

Attest:

BRUCE LEHMAN

Attesting Officer    *Commissioner of Patents and Trademarks*